US00PP18053P2

(12) United States Plant Patent
Meyer

(10) Patent No.: US PP18,053 P2
(45) Date of Patent: Sep. 18, 2007

(54) ***PETUNIA* PLANT NAMED 'BALSUNHOPI'**

(50) Latin Name: *Petunia×hybrida*
Varietal Denomination: Balsunhopi

(75) Inventor: Kerry M. Meyer, St. Thomas, MO (US)

(73) Assignee: Ball Horticultural Company, West Chicago, IL (US)

( * ) Notice: Subject to any disclaimer, the term of this patent is extended or adjusted under 35 U.S.C. 154(b) by 89 days.

(21) Appl. No.: 11/298,064

(22) Filed: Dec. 9, 2005

(51) Int. Cl.
*A01H 5/00* (2006.01)

(52) U.S. Cl. ..... Plt./356
(58) Field of Classification Search ..... Plt./263, Plt./356
See application file for complete search history.

*Primary Examiner*—Howard J. Locker
(74) *Attorney, Agent, or Firm*—Audrey Charles

(57) ABSTRACT

A new and distinct cultivar of *Petunia* plant named 'Balsunhopi' characterized by its dark pink-colored flowers, dark green-colored foliage, excellent branching, and mounded, trailing growth habit.

1 Drawing Sheet

Latin name of genus and species of plant claimed: *Petunia×hybrida.*
Variety denomination: 'Balsunhopi'.

BACKGROUND OF THE INVENTION

The present invention relates to a new and distinct cultivar of *Petunia* plant botanically known as *Petunia×hybrida* and hereinafter referred to by the cultivar name 'Balsunhopi'.

The new cultivar originated in a controlled breeding program in Arroyo Grande, Calif. during June 2002. The objective of the breeding program was the development of *Petunia* cultivars having single-type flowers with unique colors and vigorous, mounded, and trailing growth habit.

The female (seed) parent of the new cultivar was the proprietary *Petunia×hybrida* breeding selection designated 054-10, not patented, characterized by its striped violet and white-colored flowers, dark green-colored foliage, and mounded, trailing growth habit. The male (pollen) parent of the new cultivar was 'Kakegawa S57', U.S. Plant Pat. No. 14,007, characterized by its lavender-colored flowers, medium green-colored foliage, and mounded, spreading growth habit. The new *Petunia* was discovered and selected by the inventor as a single flowering plant within the progeny of the above stated cross-pollination during March 2003 in a controlled environment in Arroyo Grande, Calif.

Asexual reproduction of the new cultivar by terminal stem cuttings since March 2003 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balsunhopi' as a new and distinct cultivar of *Petunia* plant:

1. Dark pink-colored flowers;
2. Dark green-colored foliage;
3. Excellent branching; and
4. Mounded, trailing growth habit.

Plants of the new cultivar differ from plants of the female parent primarily in flower color and from plants of the male parent primarily in flower color, foliage color, and growth habit.

Of the many commercially available *Petunia* cultivars known to the inventor, the most similar in comparison to the new cultivar is 'Kakegawa S59', U.S. Plant Pat. No. 13,979. However, in side by side comparisons, plants of the new cultivar differ from plants of 'Kakegawa S59' in the following characteristics:

1. Plants of the new cultivar have larger flowers than plants of 'Kakegawa S59'; and
2. Plants of the new cultivar have a slightly different flower color from plants of 'Kakegawa S59'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsunhopi'. The plants were grown in 10 cm pots for 10 weeks in a greenhouse at West Chicago, Ill.

DETAILED BOTANICAL DESCRIPTION

Figure 1:
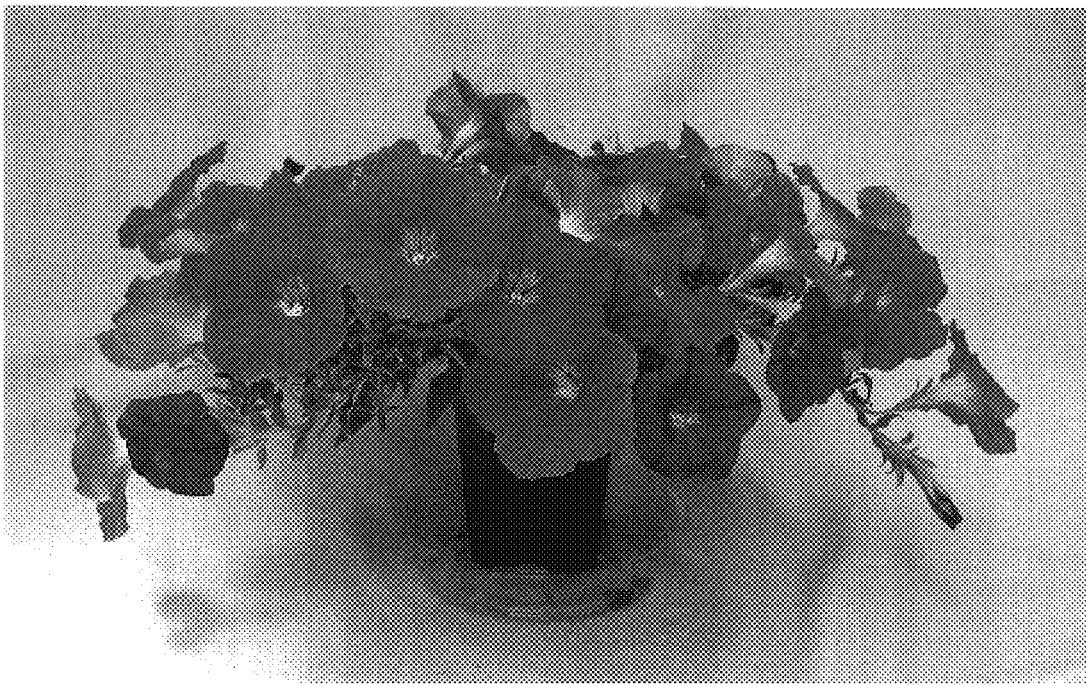
FIG. 1 illustrates a side view of the overall growth and flowering habit of 'Balsunhopi'.
Figure 2:
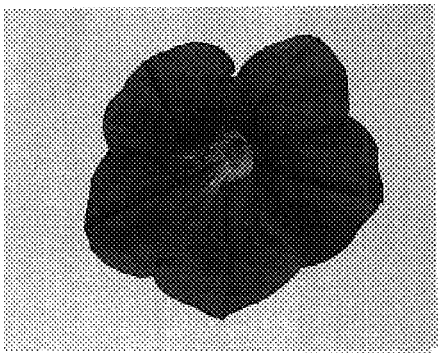
FIG. 2 illustrates a close-up view of an individual flower of 'Balsunhopi' when first open.
Figure 3:
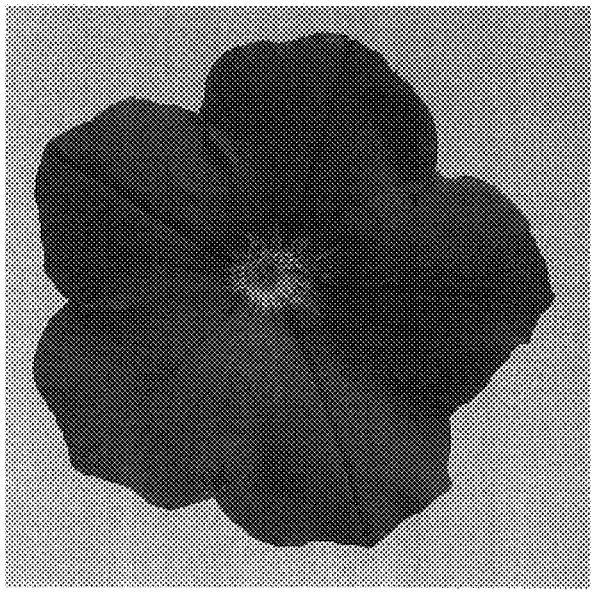
FIG. 3 illustrates a close-up view of an individual flower of 'Balsunhopi' when fully open.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 27, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 10 weeks utilizing a soilless growth medium. Greenhouse temperatures were maintained at approximately 58° F. to 75° F. (14° C. to 24° C.) during the day and approximately 52° F. to 62° F. (11° C. to 17° C.) during the night. Greenhouse light levels of 5,000 to 8,000 footcandles were maintained during the day.

Botanical classification: *Petunia×hybrida* cultivar Balsunhopi.

Parentage:

*Female parent.*—Proprietary *Petunia×hybrida* breeding selection designated 054-10, not patented.

*Male parent.*—'Kakegawa S57', U.S. Plant Pat. No. 14,007.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Crop time.*—Approximately 6 to 8 weeks from a rooted cutting.

*Growth habit and general appearance.*—Mounded, trailing.

*Size.*—Height from soil level to top of plant plane: Approximately 12.9 cm. Width: Approximately 41.8 cm.

*Branching habit.*—Freely basal branching. Approximately 5 main branches per plant with lateral branches forming at every node.

*Branch.*—Strength: Moderate to strong. Length: Approximately 17.0 cm. Diameter: Approximately 3.5 mm. Texture: Densely pubescent with soft, medium length hairs. Color of mature stem: 144A. Internode length at center of branch: Approximately 2.4 cm.

*Foliage.*—Number of leaves per main branch: Approximately 14. Fragrance: Slight. Form: Simple. Arrangement on flowering stem: Opposite. Aspect: Perpendicular or obtuse angle to stem. Shape: Ovate. Margin: Entire. Apex: Acute. Base: Attenuate, sessile. Venation pattern: Pinnate. Length of mature leaf: Approximately 5.2 cm. Width of mature leaf: Approximately 2.4 cm. Texture of upper and lower surfaces: Densely pubescent with short length hairs. Color of upper surface of mature foliage: 147A with venation of 143C. Color of lower surface of mature foliage: 147B with venation of 143C. Petiole length: Approximately 4.6 mm. Petiole diameter: Approximately 2.9 mm. Petiole texture: Densely pubescent. Petiole color: 143C.

Flowering description:

*Flowering habit.*—'Balsunhopi' is freely flowering under outdoor growing conditions with substantially continuous blooming from spring through autumn and year round in greenhouse environment.

*Time to first flower.*—Approximately 8.5 weeks after sticking of unrooted cutting.

*Lastingness of individual bloom.*—Approximately 5 to 7 days.

Flower description:

*Type.*—Simple, salverform. Quantity per plant at ten weeks: Approximately 22.

*Bud rate of opening.*—Generally takes 1 to 2 days for bud to progress from first color to fully open flower.

*Bud just before opening.*—Quantity per plant at ten weeks: Approximately 23. Shape: Oblong. Length: Approximately 4.6 cm. Diameter at apex: Approximately 8.4 mm. Diameter at base: Approximately 4.8 mm. Texture: Densely pubescent. Color of petals: Closest to N81A. Color of tube: 145C with venation of 79A.

*Corolla.*—Diameter: Approximately 6.7 cm.

*Petals.*—Quantity: 5 fused to form a tube. Shape: Obovate. Apex: Acute. Margin: Entire, ruffled. Appearance: Velvety. Texture of upper and lower surfaces: Glabrous. Length of petal from tube: Approximately 3.3 cm. Length of free portion of petal: Approximately 1.6 cm. Petal width: Approximately 3.7 cm. Color of upper surface when first open: 61B. Color of upper surface when fully open: Closest to 67A with edges of 67C and fades with age to N81A. Color of lower surface when first open and fully open: N66C with venation of 145A.

*Corolla tube.*—Length: Approximately 3.6 cm. Diameter at distal end: Approximately 1.5 cm. Diameter at proximal end: Approximately 2.9 mm. Texture of inner surface: Glabrous. Texture of outer surface: Lanate. Color of inner surface: 150D with venation of 79A. Color of outer surface: 150D with venation of both 79A and 144B.

*Peduncle.*—Strength: Strong. Aspect: Acute angle to stem. Length: Approximately 2.5 cm. Diameter: Approximately 2.0 mm. Texture: Densely pubescent. Color: 144B.

*Sepals.*—Quantity per flower: 5 fused along lower half. Shape: Linear. Apex: Acute. Sepal length: Approximately 2.2 cm. Sepal width: Approximately 3.1 mm. Texture of upper and lower surfaces: Densely pubescent. Color of upper and lower surfaces: 143A at apex, transitioning to 143C at base.

*Reproductive organs.*—Androecium: Stamen quantity: 5 fused to inside of corolla tube. Stamen length: Approximately 2.7 cm. Length of free portion of filament: Approximately 1.7 cm. Filament color: 145C with 70D at tip. Anther shape: Bilobed. Anther length: Approximately 1.5 mm. Anther color: 5D. Pollen amount: Abundant. Pollen color: 11D. Gynoecium: Pistil quantity: One per flower. Pistil length: Approximately 2.9 cm. Stigma shape: Funnel. Stigma length: Approximately 2.5 mm. Stigma color: 143B. Style length: Approximately 2.3 cm. Style color: 145C. Ovary diameter: Approximately 4.0 mm. Ovary color: 144B.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balsunhopi', substantially as herein shown and described.

* * * * *